United States Patent [19]

Eggli

[11] Patent Number: Plant 7,547

[45] Date of Patent: Jun. 4, 1991

[54] *SEQUOIA SEMPERVIRENS* TREE NAMED 'EGGLII PROSTRATA'

[76] Inventor: Jules Eggli, 514 Cornell Ave., San Mateo, Calif. 94402

[21] Appl. No.: 372,254

[22] Filed: Jun. 27, 1989

[51] Int. Cl.[5] ..... A01H 5/00

[52] U.S. Cl. ..... Plt./50

[58] Field of Search ..... Plt./50

[56] References Cited

PUBLICATIONS

Don Ouden, P., "*Sequoia*" *The International Book of Trees*, Pub.: KOMT, The Hague 1965, pp. 380–382.

Taylor, G., et al., (Eds.) "The Dwarf Conifers", *The Conifers*, Simon and Schuster, 1973, pp. 118, 119.

*Primary Examiner*—James R. Feyrer

*Attorney, Agent, or Firm*—Flehr, Hohbach, Test, Albritton & Herbert

[57] ABSTRACT

A new and distinct variety of *Sequoia sempervirens* Egglii Prostrata characterized particularly but its prostrate growth characteristics, and its main stem branching at a low height relative to the ground surface.

3 Drawing Sheets

1

This invention relates to a new and distinct variety of *Sequoia sempervirens* herein referred to as "*Sequoia sempervirens* Egglii Prostrata." *Sequoia sempervirens* Egglii Prostrata was discovered by Mr. Jules Eggli as a newly found seedling of *Sequoia sempervirens* at Eggli Nursery, owned by Mr. Eggli and located at 110 East 25th Avenue, San Mateo, Calif. 94403.

*Sequoia sempervirens* Egglii Prostrata was found growing in Egglii Nursery in 1974 amongst approximately 10,000 *sempervirens* seedlings. The parentage is unknown. However, it is believed to be the result of a random mutation of a *Sequoia sempervirens* seedling.

The 10,000 seedlings were grown from seeds originally planted in pots during 1974. *Sequoia sempervirens* Egglii Prostrata was first recognized as a new and distinct variety in 1974 when it was observed that, unlike the wild-type *Sequoia sempervirens* seedlings, the Egglii Prostrata variety did not grow erect but grew prostrate. Thus, this new variety of *Sequoia sempervirens* produces an attractive and highly useful ground-cover. Other characteristics of *Sequoia sempervirens* Egglii Prostrata which distinguish it from wild-type *Sequoia sempervirens* will be described in more detail hereinafter.

The plant was first asexually propagated by cuttings in 1976 taken by Mr. Eggli at his nursery in San Mateo. Approximately 500 sports have been asexually propagated.

Figure 1:
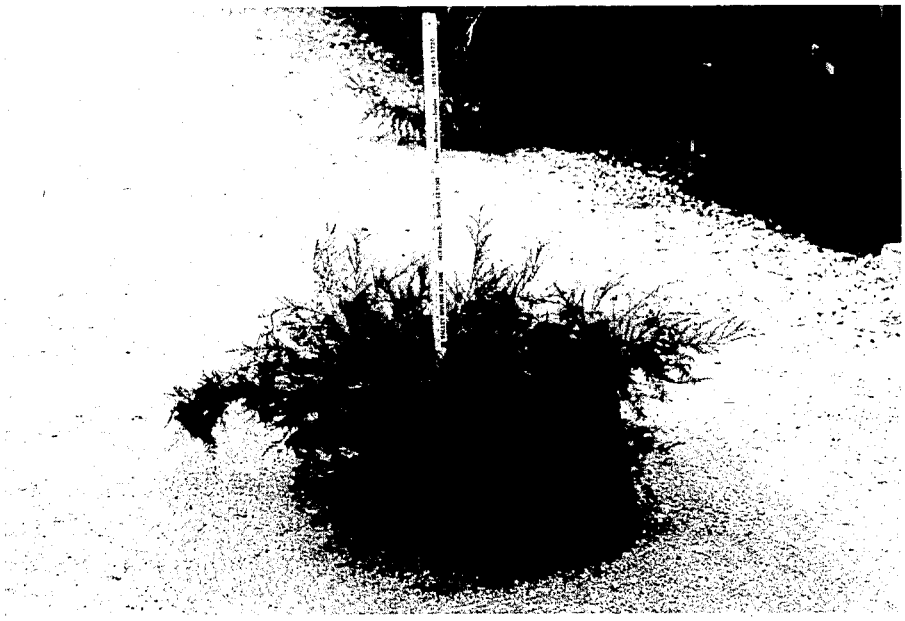
Figure 2:
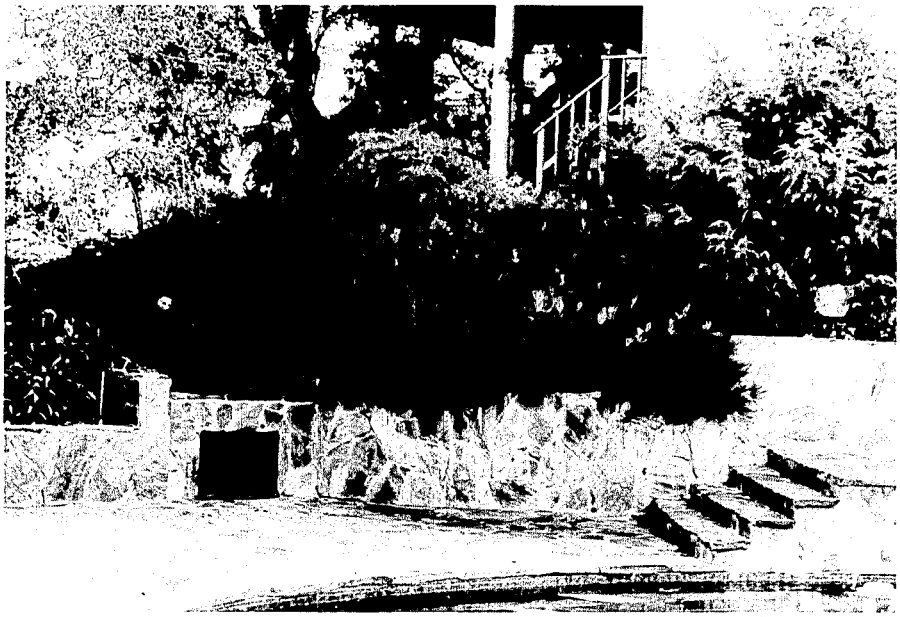

An outstanding characteristic of the new variety is that it does not grow erect but grows prostrate (see FIGS. 1 and 2). Field trials indicate that after ten years, in good soil conditions, the plant grows to a height of 1½ feet to approximately 3½ feet with a spread of 6 to 12 feet, thus producing a beautiful and highly useful ground cover. The new variety is resistant to all but heavy winds, is disease resistant and extremely fire resistant. Therefore, the new variety of *Sequoia sempervirens* has unique advantages for use as a fire resistant ground-cover.

FIG. 1 of the accompanying drawings shows the newly discovered variety of the invention planted in a pot, after 8 years of growth.

2

FIG. 2 shows five asexually propagated cuttings of the new variety, planted in the ground, after 10 years of growth.

Figure 3:
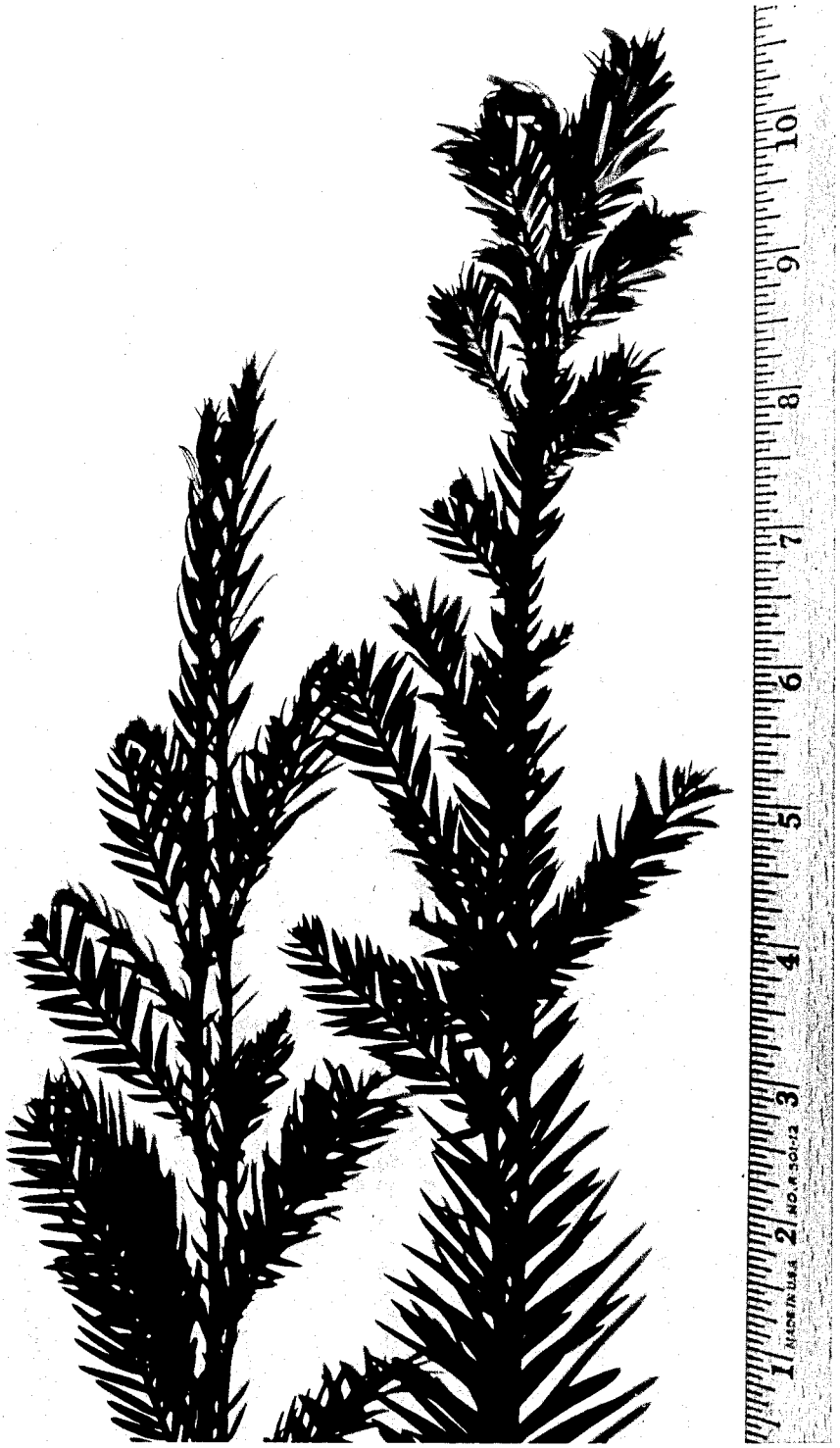

FIG. 3 shows two branches taken from a 10 year-old Egglii Prostrata each of which demonstrates characteristic new growth. The top branch shows new growth as a linear extension of the main branch. The bottom branch in FIG. 3 depicts a typical branching pattern produced after main branch elongation.

The following is a detailed description of the new variety.

Locality where grown and observed: 110 East 25th Avenue San Mateo, Calif.

Parentage: Probable mutation of *Sequoia sempervirens* seedling.

Propagation: Holds its distinguishing characteristics through succeeding propagations by cuttings. Of the approximately 500 sports so far propagated asexually, approximately 25 (5%) of the sports sprout a single upward shoot approximately four to five years after propagation. This upward shoot emanates from a nodule at the terminus of the vertical trunk from which most of the main branches radiate. The vertical shoot can be easily and quickly removed with shears and has not been independently propagated to determine its characteristics. Those few plants which exhibit this phenomenon do so only after the prostrate form of this new and distinct variety has manifested itself.

Form: Prostrate; after 10 years growth, approximately 1½ to 3½ feet in height; compact with a symmetrical spread of approximately 6 to 12 feet if grown in an open area; vigorous and very robust with lush, green foliage.

Rate of growth: Approximately 2 foot spread after two years from ground planting in good soil.

Time to maturity: Unknown.

Trunk: The trunk stands approximately one foot above the ground after approximately eight years of growth. A single plant observed after 10 years of growth has a trunk height of about 12 inches. The trunk of this latter plant at six inches above the ground has a diameter of about 1¼ inches. A nodule type structure forms the terminus of the trunk from which most of the substantially horizontal branches radiate. Occasional individual branches extend substantially horizontally from the trunk just below the terminal nodule. The terminal nodule is typically observed about 10 to 12 inches above the ground when the plant is from 8 to 10 years old. The bark of the trunk has the same characteristics as wild-type *Sequoia sempervirens* including texture and color when compared at the same age.

Branches: The plant, observed at the end of eight or ten years, has a unique branching pattern. Wild-type *Seqouia sempervirens* typically has a main stem growing to a height of many feet with main branches growing therefrom at intervals. *Sequoia sempervirens* Egglii Prostrata is distinguishable from the wild-type in that the primary branches emanate from the terminal nodule atop the main stem trunk which is located approximately 10 to 12 inches above the ground in 8 to 10 year-old plants. Such primary branches in the 8 to 10 year-old plant are approximately ½ to ¾ inches in diameter near the juncture with the nodule or trunk. Generally, five to seven and sometimes five to nine primary branches emanate from the trunk nodule. The main branches are approximately 3 to 6 feet long; side laterals vary in length from over a few inches to over a foot long. Some laterals are located opposite each other and others are alternate.

*Color.*—The main branches close to the trunk have a texture and coloration similar to that of the trunk and that found in the wild type *Sequoia sempervirens.* This part of the branch represents old growth. The branch portion located distally from the old growth branch gradually turns from the old growth branch color and texture to a branch having mature characteristics. Such characteristics include relatively smooth texture and a green color substantially the same as that found for the mature form for the leaves (needles) and most closely corresponding to Green Group 137A FAN3 of The RHS Colour Chart from The Royal Horticultural Society on London. New growth, when observed, is located distally from the mature stem. This new growth branch has a smooth texture and has a color substantially the same as new growth leaves (needles) associated therewith. This color corresponds most closely to Yellow-Green Group 144A as set forth in FAN3 of The RHS Colour Chart. FIG. 3 shows the typical branch structure and color of *Sequoia sempervirens* Egglii Prostrata.

Foliage:

*Leaves.*—Evergreen; glabrous: needle; sessile.

*Length of leaves.*—Approximately one-half of an inch to one inch.

*Width of leaves.*—Approximately one-tenth to one-quarter of an inch.

*Rib.*—One mid-rib full length of leaf.

*Leaf arrangement.*—Alternate; non decussate, spaced 1/16 to ¼ of an inch apart.

*Color.*—The upper surface of new shoots are Yellow-Green Group 144A FAN3 of The RHS Colour Chart, mature shoots Green Group 137A FAN3 of The RHS Colour Chart. The color of the lower surfaces are similar to that observed for wild-type *Sequoia sempervirens* (California Coast Redwood).

Flower or other reproductive organs: Unknown; none observed.

Weather resistance: Grows well in coastal areas of California.

Exposure to wind: Resistant to all but very heavy winds.

Disease resistance: Very disease resistant.

Other characteristics: Likes acid soils but will grow in many types of soil. Extremely fire resistant.

Having described and illustrated the new and distinct variety *Sequoia sempervirens* Egglii Prostrata, what is claimed is:

1. A new and distinct variety of *Sequoia sempervirens* Egglii Prostrata substantially as illustrated and described, characterized particularly by its prostrate growth characteristics, and its main stem branching at a low height relative to the ground surface as compared to wild-type *Sequoia sempervirens.*

* * * * *